United States Patent [19]

Pearson

[11] Patent Number: 5,490,610
[45] Date of Patent: Feb. 13, 1996

[54] SEMI-AUTOMATED MEDICATION DISPENSER

[76] Inventor: Walter G. Pearson, P.O. Box 4371, Pineville, La. 71361

[21] Appl. No.: 421,456

[22] Filed: Apr. 13, 1995

Related U.S. Application Data

[63] Continuation of Ser. No. 206,877, Mar. 7, 1994, abandoned.
[51] Int. Cl.⁶ ................................................. G07F 11/00
[52] U.S. Cl. ........................................... 221/2; 221/211
[58] Field of Search ......................... 221/7, 9, 15, 211, 221/278, 127, 126, 2

[56] References Cited

U.S. PATENT DOCUMENTS

| | | | |
|---|---|---|---|
| 2,684,783 | 7/1954 | Ahlstrom | 221/258 |
| 3,334,784 | 8/1967 | Morrison | 221/7 |
| 3,467,277 | 9/1969 | Tolliver | 221/264 |
| 3,848,112 | 11/1974 | Weichselbaum et al. | 235/61.7 R |
| 3,892,489 | 7/1975 | Wdzieczkowski | 356/157 |
| 3,917,045 | 11/1975 | Williams et al. | 194/4 C |
| 4,018,358 | 4/1977 | Johnson et al. | 221/7 |
| 4,141,461 | 2/1979 | LaChance | 220/253 |
| 4,267,942 | 1/1981 | Wick, Jr. et al. | 221/2 |
| 4,473,884 | 9/1984 | Behl | 364/479 |
| 4,546,901 | 10/1985 | Buttarazzi | 221/10 |
| 4,655,026 | 4/1987 | Wigoda | 53/55 |
| 4,664,289 | 5/1987 | Shimizu et al. | 221/2 |
| 4,674,651 | 6/1987 | Scidmore et al. | 221/3 |
| 4,674,652 | 6/1987 | Aten et al. | 221/3 |
| 4,695,954 | 9/1987 | Rose et al. | 364/413 |
| 4,733,362 | 3/1988 | Haraguchi | 364/479 |
| 4,785,969 | 11/1988 | McLoughlin | 221/2 |
| 4,832,229 | 5/1989 | Hackmann et al. | 221/25 |
| 4,847,764 | 7/1989 | Halvorson | 364/413.02 |
| 4,853,521 | 8/1989 | Claeys et al. | 235/375 |
| 4,911,327 | 3/1990 | Shepherd et al. | 221/3 |
| 4,939,705 | 7/1990 | Hamilton et al. | 368/10 |
| 4,967,928 | 11/1990 | Carter | 221/2 |
| 4,971,221 | 11/1990 | Urquhart et al. | 221/2 |
| 5,097,982 | 3/1992 | Kedem et al. | 221/126 |
| 5,292,029 | 3/1994 | Pearson | 221/2 |
| 5,405,048 | 4/1995 | Rogers et al. | 221/211 |

Primary Examiner—Kenneth Noland
Attorney, Agent, or Firm—John H. Runnels

[57] ABSTRACT

A semi-automated medication dispenser is disclosed that greatly simplifies the logistics of correctly dispensing multiple medications to multiple patients in the correct dosages at the correct times, in a manner that is cost-efficient and labor-efficient, that greatly reduces the probability of errors, and that inhibits pilferage. The novel dispenser can be loaded with many days' worth of medication (e.g., 30 days) at one time, and requires no special packaging for the medications. The novel dispenser is controlled by a computer. Patient information and physician orders are entered into the computer's memory. Medications needed by all the patients in a ward are loaded into individual compartments, for example by a pharmacist. Many days' worth of medication may often be loaded at once. After the medications are loaded into the dispenser, access to the individual compartments is controlled by the computer. When a proper password is entered—for example by the dispensing nurse—followed by identifying information for a particular patient, the computer allows access to only those compartments containing medications that are appropriate for the individual patient at that time. In many cases, the computer controls the dosage of the medication being dispensed as well, by controlling the number of pills dispensed. Thus each patient receives all appropriate medications, and only the appropriate medications. The computer also simultaneously makes a record of the medications administered to each patient. In the entire process, human hands need never touch the tablets or capsules being dispensed to the patient.

6 Claims, 3 Drawing Sheets

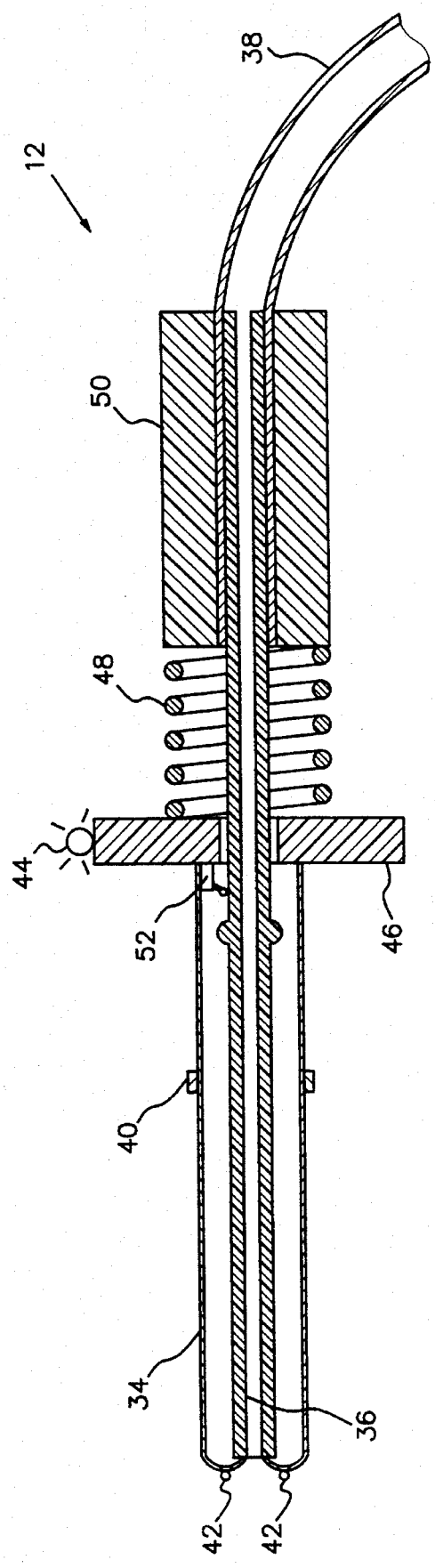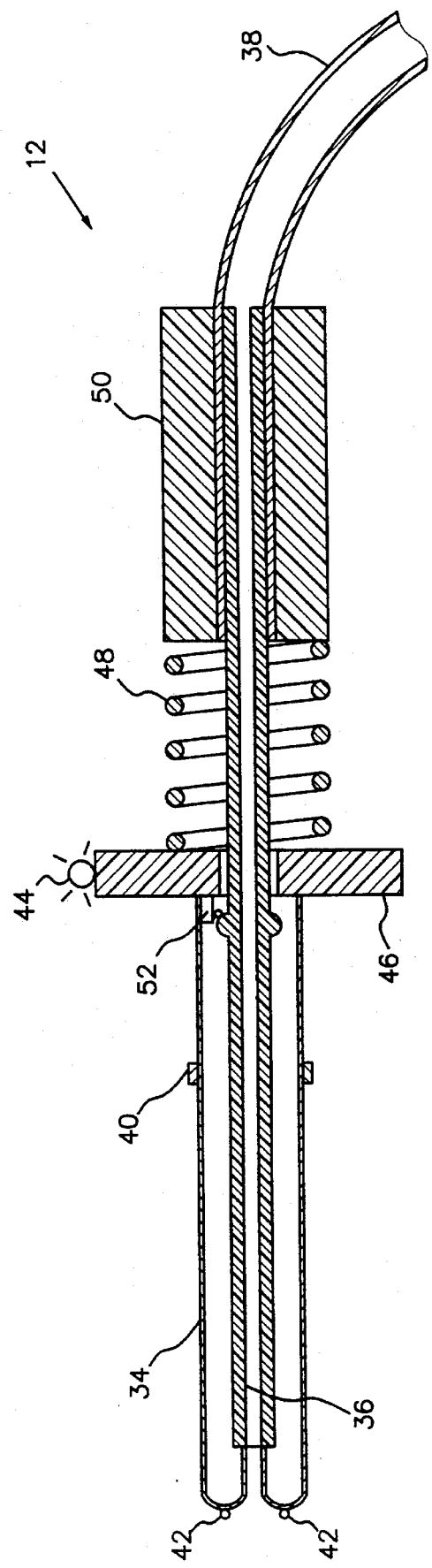

5,490,610

SEMI-AUTOMATED MEDICATION DISPENSER

This application is a continuation of application Ser. No. 08/206,877, filed Mar. 7, 1994 now abandoned.

This invention pertains to semi-automated medication dispensers, particularly to medication dispensers suitable for dispensing multiple medications to multiple patients with minimal risk of error and minimal risk of pilferage.

Hospitals, clinics, nursing homes, and the like typically must dispense multiple medications to multiple patients on ever-changing schedules. Insuring that the right patient receives the right amount of the right medication at the right time presents significant logistical problems to the personnel responsible for prescribing, dispensing, and administering the medications. Even when everything in the system works properly, the logistics and paperwork required to dispense all medications to a group of patients correctly can be very time-consuming, labor-intensive, and expensive.

Unfortunately, it is not uncommon for medications to be administered to the wrong patient, or to the right patient in the wrong amount or at the wrong time. Such mistakes can arise in many ways. A patient may be misidentified, or moved to a different bed. Busy nurses may neglect to cross-check patient identification numbers in all cases. The cups containing different patients' medications may inadvertently be switched. The potentially harmful consequences of incorrectly dispensing medications to patients requires no elaboration.

Compounding these already-difficult logistical problems is the fact that a clandestine demand exists for many prescription drugs, requiring that appropriate security measures be taken to minimize the risk of theft.

U.S. Pat. No. 3,848,112 discloses magnetically coded identification tags for correlating the identity of a patient to the patient's prescriptions, samples, and the like.

U.S. Pat. No. 4,695,954 discloses a medication dispensing system for use with a single patient, in which all medications to be dispensed at a particular time for that patient are manually loaded into a particular compartment of the device, and the device allows access to each compartment at the appropriate time.

U.S. Pat. No. 4,971,221 discloses a drug dispenser with a monitor such as an optical sensor to detect when a dose of the drug has been dispensed.

U.S. Pat. No. 4,967,928 discloses a medication cart with an on-board computer system in which unsecured medications are stored in conventional cabinet cubicles; and in which secured narcotics are either stored in a single-dose, automatic dispenser apparatus requiring special packaging for dispensing doses of the narcotics, or are stored in a locked conventional cubical.

U.S. Pat. No. 3,917,045 discloses an automatic drug dispensing apparatus which dispenses drugs from cartridges, each of which holds a plurality of individual drug dosages.

U.S. Pat. No. 4,847,764 discloses a system for dispensing medications in a health care institution in which a central computer system controls a plurality of remote medication dispensers.

Other patents cited during the prosecution of the "parent," "grandparent," and "great-grandparent" applications of the present continuation-in-part application include the following: U.S. Pat. Nos. 2,684,783; 3,334,784; 3,467,277; 3,892,489; 4,018,358; 4,141,461; 4,267,942; 4,546,901; 4,473,884; 4,655,026; 4,664,289; 4,674,651; 4,674,652; 4,733,362; 4,785,969; 4,832,229; 4,853,521; 4,911,327; and 4,939,705.

There is a continuing, unfilled need for a multi-patient, multi-medication, semi-automated medication dispenser that can correctly dispense the correct medications to the correct patients at the correct times in the correct dosages, in any sequence of patients that is convenient, in a manner that is cost-efficient, that reduces the amount of human labor required, that minimizes the risk of error, that does not require any special packaging for pills dispensed, and that is resistant to pilferage.

A novel, semi-automated medication dispenser has been invented that greatly simplifies the logistics of correctly dispensing multiple medications to multiple patients in the correct dosages at the correct times, in a manner that is cost-efficient and labor-efficient, that greatly reduces the probability of errors, and that inhibits pilferage. The novel dispenser can be loaded with many days' worth of medication (e.g., 30 days) at one time, and requires no special packaging for the medications.

The novel dispenser is controlled by a computer. Patient information and physician orders are entered into the computer's memory. Medications needed by all the patients in a ward are loaded into individual compartments, for example by a pharmacist. Many days' worth of medication may often be loaded at once.

After the medications are loaded into the dispenser, access to the individual compartments is controlled by the computer. When a proper password is entered—for example by the dispensing nurse—followed by identifying information for a particular patient, the computer allows access to only those compartments containing medications that are appropriate for the individual patient at that time. In many cases, the computer controls the dosage of the medication being dispensed as well, by controlling the number of pills dispensed. Thus each patient receives all appropriate medications, and only the appropriate medications. The computer also simultaneously makes a record of the medications administered to each patient. In the entire process, human hands need never touch the tablets or capsules being dispensed to the patient.

BRIEF DESCRIPTION OF THE DRAWINGS

FIGS. 3a and 3b illustrate two positions of a suction tube that may be used in conjunction with this invention.

One embodiment of the present invention is illustrated in FIGS. 1–3. FIG. 1a illustrates a longitudinal view of a medication-dispensing cart in accordance with the present invention, and FIG. 1b illustrates a partial cross-sectional view of the same cart. The cart 2 preferably has optional wheels or casters 4, or other means of locomotion to make it mobile. Alternatively, the wheels could be omitted, and the cart could be stationary. Optional handles 6 on either end of the cart allow the cart to be maneuvered easily. There are a number of containers 8 and drawers 10 for holding medications. A suction tube 12 is used to withdraw pills and tablets from containers 8, as is explained further below.

Figure 1B:
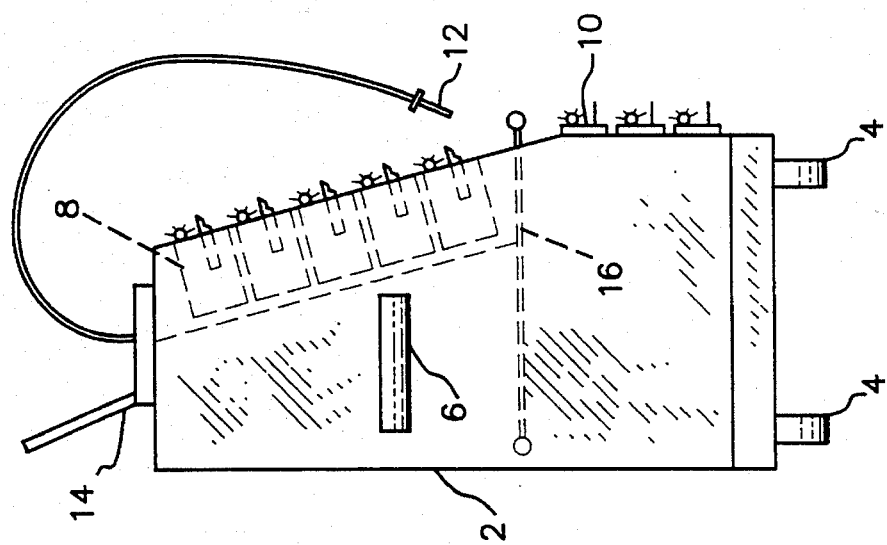
FIG. 1b illustrates a partial cross-sectional view of the same cart.

A computer 14 is shown schematically. ("Computer" is used in the specification and the claims in a broad sense, and would include, for example, a microprocessor or a microcontroller, along with associated memory elements and input/output devices such as are known in the art of electronics today.) Not shown are various input/output devices and connections for the computer whose operation and construction will be understood by those of skill in the art in electronics after reading the present disclosure. Input/output devices for the computer may include, for example, a keyboard, trackball, and/or mouse used by the operator of the cart, a port for uploading/downloading data to or from another computer, a modem for uploading/downloading data to or from another computer via a telephone line, a monitor, a printer, and various input/output connections between the computer and the devices that it controls, such as the containers 8, drawers 10, and suction tube 12.

Metal lid 16 slides out of the way into cart 2, between containers 8 and drawers 10, when the cart is in use. When the cart is not in use, metal lid 16 may be slid forward, and swung on a hinge or pivot up and over containers 8. Lid 16 may then by physically locked over containers 8, in a configuration not illustrated, to prevent unauthorized access to the medications in the containers. (Drawers 10 are automatically locked by the computer at all times except when the computer specifically allows access.) Thus all medications contained in the cart are locked away to prevent unauthorized access when the cart is not in use. As a further precaution, it is preferred that the cart also be placed in a locked room when not in use. The cart may optionally be equipped with a motion sensor to sound an alarm if the cart is moved without an appropriate password first being entered into the computer. Note that closing lid 16 also has the benefit of inhibiting contamination of the drugs within the containers 8 by dust or the like.

Figure 2:
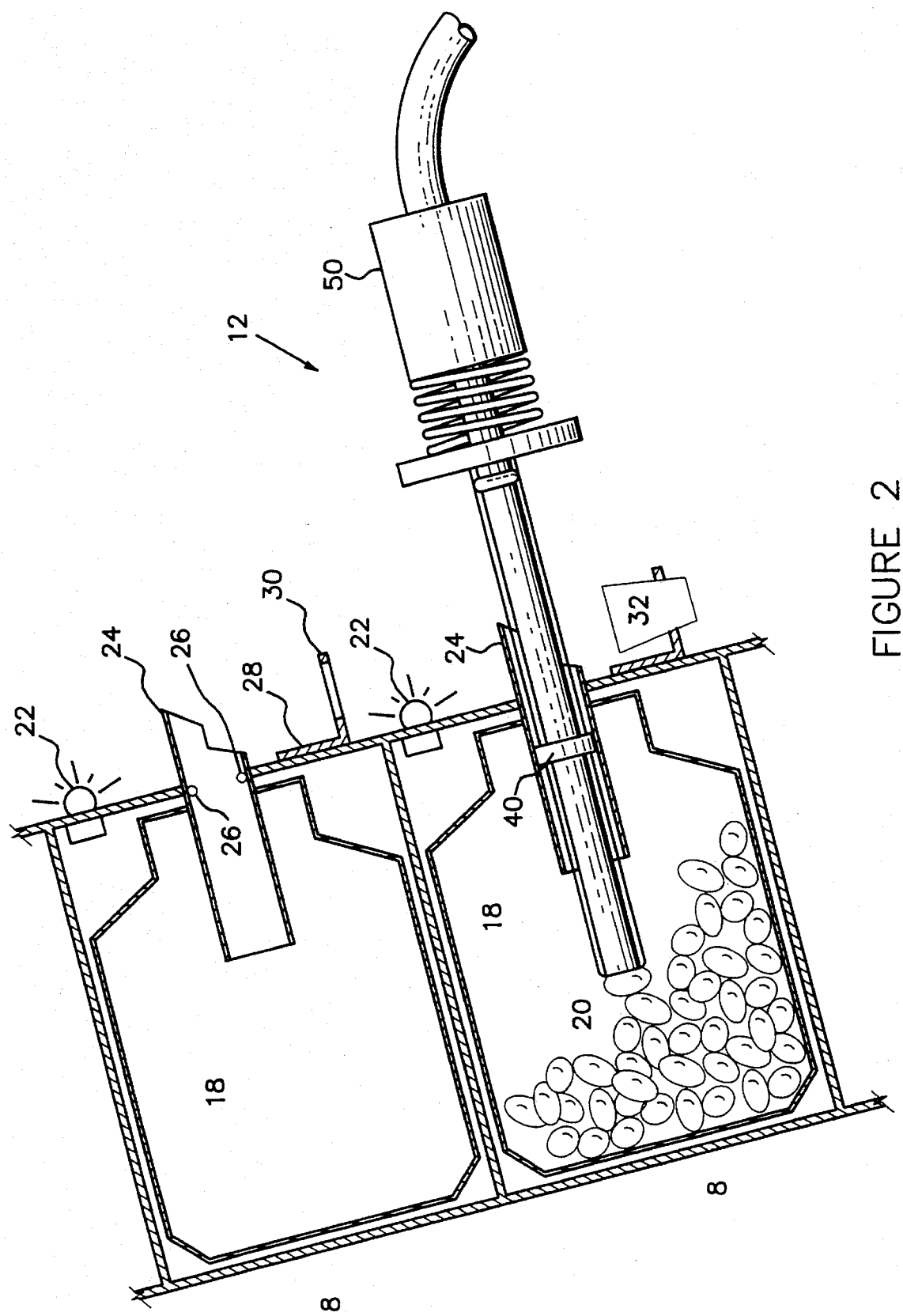
FIG. 2 illustrates a cross-section of two containers used in the cart.

FIG. 2 illustrates a cross-section of two containers 8. The upper container is shown empty except for medication jar 18, while the lower container contains tablets or capsules of medication 20 in jar 18. Suction tube 12 is shown entering the lower container to withdraw one or more tablets or capsules 20. Each container 8 is adapted to hold a bottle or jar 18 holding the capsules or tablets 20. Alternatively, there need be no bottle or jar, and the capsules or tablets may be placed directly in the container. Each container 8 has a signal light 22, which may for example be either red or green. The container has a plastic tube orifice 24 to allow entry and exit of suction tube 12; the tube orifice preferably has a lip on the upper surface as illustrated, to facilitate dropping an extracted pill into a paper cup as described below. The tube orifice also has a fiber optic or other sensor (such as a microswitch) 26 to indicate when an authorized or unauthorized entry is made into the container; in the case of an unauthorized entry, it may be desirable to have an alarm sound to indicate that a possible theft is in progress. The exterior of each container has a label holder 28 to identify the medication that it contains, and preferably has a platform 30 to hold a collection cup 32.

Figure 1A:
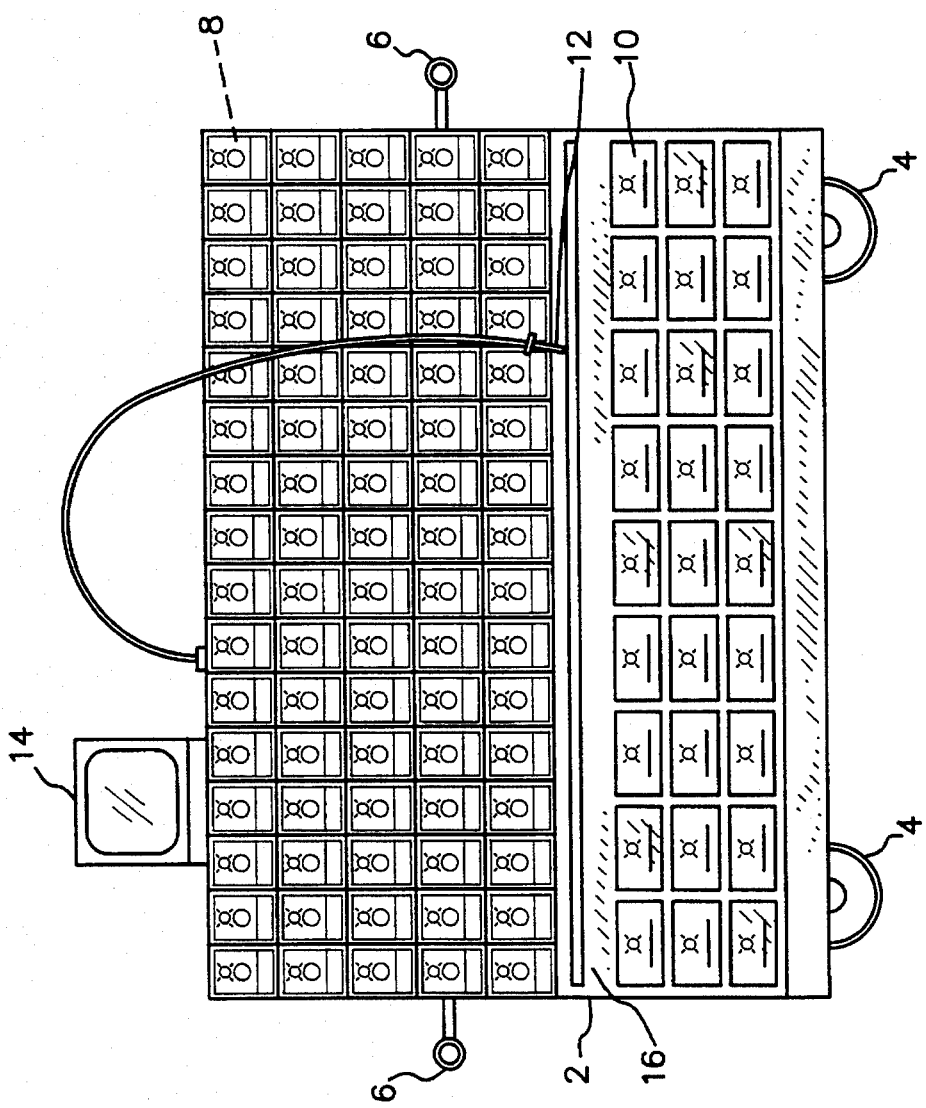
FIG. 1a illustrates a longitudinal view of a medication-dispensing cart in accordance with the present invention.

FIGS. 3a and 3b illustrate the suction tube 12 in greater detail. An outer sheath 34 made of a flexible clear plastic covers part of the structure. Inner cylinder 36, which picks up a pill, is connected via rubber hose 38 to a suction motor (not shown) inside cart 2. Alternatively, the suction tube need not be connected to the cart as illustrated in FIG. 1a, but could instead be part of a portable unit containing a small vacuum motor in the handle. Glide collar 40 positions the inner cylinder in the tube orifice 24 when the inner cylinder is inserted in a container, and allows freedom of rotation to allow the inner cylinder 36 to find a pill within the container. The assembly allows fiber optic (or other) sensor 42 at the end of the sheath to be pushed over the end of inner cylinder 36 to confirm whether a tablet has been picked up; if so, a signal is sent to the computer indicating success, and causing indicator light 44 to turn on. Handle plate 46 is attached to sheath 34, and slides over inner cylinder 36. As depicted in FIG. 3b, pushing on handle plate 46 pushes the end of sheath 34 over the end of inner cylinder 36 to allow the fiber optic sensor 42 to function as described. Spring 48 between handle plate 46 and handle 50 urges the handle plate back to its starting position after such an inspection. Microswitch 52 detects when the end of sheath 34 is extended past the end of inner cylinder 36 in this manner, and microswitch 52 then activates fiber optic sensors 42. Alternatively, the sheath 34, handle plate 46, and spring 48 could be omitted, and fiber optic (or other) sensors could be placed on the end of inner cylinder 36 to indicate directly when a pill has been picked up. The latter approach has the advantage of greater simplicity.

The typical operation of the invention will now be described. A nurse or other worker enters a password to be authorized to enter information, and after authorization inputs patient information and physician orders into the computer. This information may be updated as frequently as needed. The computer then compiles a list of the quantities of all needed medications for a selected period of time, which may for example be a day, a week, or a month.

A pharmacist reviews this list on a regular basis (e.g., daily, weekly), on an as-needed basis, or both, and loads the proper quantities of the indicated medications into the proper containers 8 or drawers 10. The pharmacist can simultaneously cause all containers 8 and drawers 10 to unlock by entering a password, using a mechanical key, or preferably both at the same time. Although a given medication will be located in a given compartment (or perhaps in more than one compartment if the demand for the medication is high), in many instances there will be no particular reason for segregating supplies of the same medication used by different patients. All patients taking a given drug can, in many cases, be supplied from the same container. The pharmacist confirms to the computer that each medication has been placed in the proper container or drawer, and locks the containers and drawers. The cart is then ready to be used to dispense medications to patients.

An alternative method for loading drugs into the cart is to keep the cart regularly supplied with a set of the most commonly used drugs in a particular facility, allowing the computer rather than the pharmacist to keep track of how much is dispensed to each patient (in accordance with physician orders, of course). Under this alternative, the commonly used drugs are re-stocked as their supplies get low, rather than when individual prescriptions are written. Less-commonly used drugs are still added to the cart individually by the pharmacist when prescribed by a physician.

When it is time for the medication cart to make a round, the individual responsible for dispensing the medications (usually a nurse) enters a password to be authorized to use the medication dispenser. The nurse then rolls the cart to each patient, in any convenient order; the order in which the different patients' medications are dispensed makes no difference as the dispensing is under computer control. The nurse enters identifying information for a patient—the patient's name, identification number, thumbprint, etc. After the nurse verifies that the screen displayed by the computer in fact corresponds to the correct patient, the computer unlocks each container 8 or drawer 10 holding medication that the patient is scheduled to receive at that time. The signal light 22 for each such container or drawer changes from red to green, making it easy for the nurse to identify the proper compartments.

In the case of tablets or capsules held in one of the containers 8, the nurse inserts suction tube 12 into the corresponding orifice tube 24. The sensor 26 activates the suction motor, and suction then causes the tube to pick up one pill at a time. (The inner diameter of inner cylinder 36 is preferably about 0.125 inch, smaller than the cross-section of nearly all pills used in prescription medications today, to minimize the likelihood that a pill will be sucked into the interior of the inner cylinder. Should a smaller pill size be encountered, the inner diameter could be made smaller; or an alternative method of inhibiting pills from being sucked into the inner cylinder is to place a small object, perhaps about the size and shape of a straight pin but with a blunt end, along the axis of the inner cylinder at the end that contacts the pills, to block pills from entering.) The nurse confirms that a pill has been successfully picked up by pushing slightly on handle plate 46, causing the end of sheath 34 to extend slightly over the end of inner cylinder 36, so that microswitch 52 activates sensors 42, and sensors 42 may detect the presence of a pill as previously described. The positive confirmation that a pill is being removed from the container allows the computer to keep accurate inventory of all the medications, reducing potential ambiguities in accounting that could be caused by the withdrawal of the tube without a pill. (Experience with a prototype embodiment of this invention has shown that a pill is successfully picked up by the tube on the first try about 90% of the time.)

Alternatively, sheath 34 could be eliminated, and the sensors 42 could be built into or onto the end of inner cylinder 36, so that the detection of a withdrawn pill is automatic, and does not require the extra step of pushing a sheath over the end of the inner cylinder.

When suction tube 12 is withdrawn from the orifice, the end of the tube may be wiped across the upper edge of orifice tube 24, causing the tablet or pill to fall into collection cup 32. The same cup may be used to collect all pills for the same patient. Note that under this procedure the pills need never touch human hands.

In an alternative approach, lid 16 could be eliminated, along with that part of each tube orifice 26 that is interior to its corresponding container 8. A sliding metal panel (not illustrated) on the interior of container 8 closes and locks the opening of orifice tube into container 8 at all times except when access to the container is authorized by the computer. When access is authorized, the signal light 22 for that container changes from red to green, and a solenoid unlocks and opens the sliding metal panel to allow suction tube 12 entry into container 8. After suction tube 12 is withdrawn, the sliding panel then closes and locks either automatically or manually, and a signal is given to the operator to proceed to the next authorized container 8, or to proceed to the next patient, or to end the round, as appropriate.

If a medication called for is not a tablet or capsule, then the indicator light over one of the drawers 10 will light, indicating the drawer holding the appropriate ointment, cream, liquid medication, suppository, vial, syringe, etc. The drawer is unlocked by the computer, allowing the nurse to withdraw the needed medication manually. After use, the medication is returned to the same drawer if it is susceptible of additional uses.

The dispensing nurse should preferably verify that there has been no mistake in the medication dispensed, to add a redundancy check to the system.

There are, of course, occasions when the cart should allow the dispensing nurse to request a medication that had not been scheduled in advance. For example, there might be such a request in the event of an emergency, if medication is dropped, or in the case of a PRN medication. In such a case, the computer may be allowed to dispense the requested medication, but only upon recording the time of the request, the name of the person authorizing the request, and a brief explanation of the reason for the request. The recordation of these deviations from the pre-authorized medications allows necessary flexibility, while maintaining responsibility and accountability for the exceptions.

The computer records all medications dispensed: name and amount of medication, identity of patient, time dispensed, and name of nurse. Thus record keeping is greatly facilitated. This data may be downloaded into one or more facility computers after the completion of the round if desired.

As used in the claims, the term "pill" is intended to include any solid medication, other than a powder, that is taken orally, including pills, capsules, tablets, and the like. As used in the claims, pills are held "freely" in a compartment if they lie more-or-less loosely in the compartment itself, or if they lie more-or-less loosely inside a jar or bottle contained in the compartment, but are not further contained in additional packaging such as a blister pack or other packaging surrounding the individual pills.

All patents and patent applications cited in this specification are hereby incorporated by reference in their entirety. Also incorporated by reference in their entirety are the disclosures of the following patent and patent applications: U.S. Pat. No. 5,292,029, issued Mar. 8, 1994; U.S. patent application Ser. No. 07/433,256, filed Nov. 8, 1989; and U.S. patent application Ser. No. 07/242,585, filed Sep. 12, 1988. In the event of a conflict, however, the present specification takes precedence.

I claim:

1. An apparatus for dispensing appropriate medications in pill form to each of a plurality of patients, comprising:

(a) a plurality of compartments, wherein each of said compartments is adapted to hold one or more pills freely;

(b) means for inputting to the apparatus medication orders for each of the patients;

(c) means for compiling the input patient medication orders, and for outputting the total numbers of each pill anticipated to be consumed by the patients during a selected period of time, so that the total numbers of pills of each type of medication may be placed in said compartments, with no more than one type of medication per compartment;

(d) means for authorizing an operator of the apparatus to dispense medications from the apparatus, wherein the apparatus will not dispense medications until the operator has been authorized;

(e) means for correlating the time and a patient's identity to the dosages of each pill appropriate for the patient at that time in accordance with the medication orders, and for authorizing the operator of the apparatus to have access to the said compartments containing the pills appropriate for the patient at the time; and (f) a tube connected to a partial vacuum, wherein said tube is adapted to enter each of the authorized said compartments and to retrieve a pill from each of the said compartments through the action of the partial vacuum.

2. An apparatus as recited in claim 1, additionally comprising means for confirming, while said tube remains within one of the said compartments, whether said tube has successfully retrieved a pill.

3. An apparatus as recited in claim 2, wherein said confirming means comprises an optical sensor to detect the presence of a pill by the interruption of a beam of light.

4. An apparatus as recited in claim 1, additionally comprising:
   (a) a plurality of second compartments, wherein each of said second compartments is adapted to hold a medication not in pill form;
   (b) means for outputting the total amounts of each medication not in pill form anticipated to be consumed by the patients during a selected period of time, so that the total amounts of each type of medication not in pill form may be placed in said second compartments, with no more than one type of medication per second compartment; and
   (c) means for correlating the time and a patient's identity to the dosages of each medication not in pill form appropriate for the patient at that time in accordance with the medication orders, and for authorizing the operator of the apparatus to have access to the said second compartments containing the medications not in pill form appropriate for the patient at the time.

5. An apparatus as recited in claim 1, wherein each of said inputting means, compiling means, authorizing means, and correlating means comprises a computer, or operates under the control of a computer.

6. An apparatus for dispensing appropriate medications to each of a plurality of patients, comprising:
   (a) a plurality of first compartments, wherein each of said first compartments is adapted to hold one or more pills freely;
   (b) means for inputting to the apparatus medication orders for each of the patients;
   (c) means for compiling the input patient medication orders, and for outputting the total numbers of each pill anticipated to be consumed by the patients during a selected period of time, so that the total numbers of pills of each type of medication may be placed in said first compartments, with no more than one type of medication per first compartment;
   (d) means for authorizing an operator of the apparatus to dispense medications from the apparatus, wherein the apparatus will not dispense medications until the operator has been authorized;
   (e) means for correlating the time and a patient's identity to the dosages of each pill appropriate for the patient at that time in accordance with the medication orders;
   (f) means for dispensing the proper numbers of each appropriate pill to the patient, wherein said dispensing means does not require contact between the pill and a human before the pill is consumed by the patient, and wherein the patients may be dispensed pills in any order, and wherein the order of the patients need not be selected prior to dispensing the pills;
   (g) a plurality of second compartments, wherein each of said second compartments is adapted to hold a medication not in pill form;
   (h) means for outputting the total amounts of each medication not in pill form anticipated to be consumed by the patients during a selected period of time, so that the total amounts of each type of medication not in pill form may be placed in said second compartments, with no more than one type of medication per second compartment; and
   (i) means for correlating the time and a patient's identity to the dosages of each medication not in pill form appropriate for the patient at that time in accordance with the medication orders, and for authorizing the operator of the apparatus to have access to the said second compartments containing the medications not in pill form appropriate for the patient at the time.

* * * * *